United States Patent [19]

Iizuka et al.

[11] Patent Number: 4,587,356
[45] Date of Patent: May 6, 1986

[54] PROCESS FOR THE PRODUCTION OF NUCLEAR SUBSTITUTED CINNAMOYLANTHRANILIC ACID DERIVATIVES

[75] Inventors: Kinji Iizuka, Kanbayashi; Tetsuhide Kamijo, Hirookayoshida; Ryoji Yamamoto, Kanbayashi; Hiromu Harada, Matsumoto, all of Japan

[73] Assignee: Kissei Pharmaceutical Co., Ltd., Japan

[21] Appl. No.: 654,231

[22] Filed: Sep. 25, 1984

Related U.S. Application Data

[63] Continuation-in-part of Ser. No. 577,758, Feb. 7, 1984, Pat. No. 4,486,597, which is a continuation of Ser. No. 405,159, Aug. 6, 1982, abandoned.

[51] Int. Cl.$^4$ ............................................. C07C 99/00
[52] U.S. Cl. ................................... 562/455; 562/453; 260/501.11; 544/107; 546/192; 548/400; 548/579; 514/567; 514/555
[58] Field of Search ................................ 562/453, 455; 260/501.11; 424/316, 319; 544/107; 546/192; 548/400, 579

[56] References Cited

U.S. PATENT DOCUMENTS

| | | | |
|---|---|---|---|
| 4,026,896 | 5/1977 | Harita et al. | 260/501.11 |
| 4,070,484 | 1/1978 | Harita et al. | 562/455 |
| 4,337,270 | 6/1982 | Noda et al. | 562/453 |
| 4,455,295 | 6/1984 | Hopp et al. | 548/579 |

FOREIGN PATENT DOCUMENTS

| | | | |
|---|---|---|---|
| 6135454 | 3/1980 | Japan | 562/445 |
| 5970654 | 4/1984 | Japan | 562/455 |

*Primary Examiner*—James H. Reamer
*Attorney, Agent, or Firm*—Depaoli & O'Brien

[57] ABSTRACT

The present invention provides an improved method for producing a nuclear substituted cinnamoylanthranilic acid compound.

Illustrative of the process is the reaction of 3-hydroxy-4-methoxybenzaldehyde with 2-carboxymalonanilic acid in an inert solvent medium in the presence of a molar excess of piperidine to provide a high purity intermediate salt precipitate, and the salt is treated with an acidic reagent to yeild N-(3-hydroxy-4-methoxycinnamoyl)anthranilic acid product.

12 Claims, No Drawings

PROCESS FOR THE PRODUCTION OF NUCLEAR SUBSTITUTED CINNAMOYLANTHRANILIC ACID DERIVATIVES

This patent application is a continuation-in-part of patent application Ser. No. 577,758, filed Feb. 7, 1984, now U.S. Pat. No. 4,486,597, which in turn is a continuation of patent application Ser. No. 405,159, filed Aug. 4, 1982 now abandoned.

BACKGROUND OF THE INVENTION

1. Field of the Invention

This invention relates to a novel method for the production of nuclear substituted cinnamoylanthranilic acid derivatives. More particularly, this invention relates to an improved method for the production of nuclear di-substituted cinnamoylanthranilic acid derivatives which possess antiallergic properties and thus are useful for treatment of diseases such as asthma, hay fever, atopic dermatitis and urticaria.

2. Description of the Prior Art

Nuclear substituted cinnamoylanthranilic acid derivatives such as N-(3,4-dimethoxycinnamoyl)anthranilic acid are known to exhibit strong antiallergic properties and to be useful for treatment of asthma, hay fever, atopic dermatitis and urticaria, as reported in U.S. Pat. No. 4,070,484; Allergy, 34, 213–219, (1979); and Igaku no Ayumi, 106, No. 8, 576–585 (1978).

Several methods for producing said derivatives have been also disclosed in Japanese patent application Nos. 7359/73, 42273/74, 42465/74, 43673/74, 43678/74, 158554/75, 158555/75, 158556/75, 139368/76, 38555/80, 38556/80 and 8858/81, and in U.S. Pat. No. 3,940,422. Of the methods disclosed in the above patent references, the process described in Japanese patent application No. 8858/81 can be operated with ease and efficiency, and thus this process has advantage for production on an industrial scale. The Japanese patent application No. 8858/81 invention is illustrated by the following preferred process embodiment.

A nuclear unsubstituted or substituted benzaldehyde derivative is heated with a 2-carboxymalonanilic acid derivative at 80°–100° C. for several hours in a solvent medium such as pyridine, benzene, toluene or xylene (10–20 times by weight the amount of the benzaldehyde derivative or the 2-carboxymalonanilic acid derivative) in the presence of a catalytic amount of a basic compound such as piperidine. The resultant reaction mixture is evaporated and the residue is dissolved in a small amount of an alcohol. The alcoholic solution is poured into ice-water, then hydrochloric acid is added to make the aqueous medium acidic, and the crystalline precipitate which forms is collected by filtration and recrystallized from a suitable organic solvent to yield the desired product.

Since the desired product in the above described procedure is obtained as a precipitate from an aqueous acidic solution of the evaporated reaction mixture by acidification with a mineral acid, unreacted materials and byproducts which are insoluble in an aqueous acidic solution are also precipitated, and these components are difficult to remove by recrystallization and thus are contained in the desired product. Hence, the desired product purified by recrystallization always contains such impurities and is not applicable for medicinal purposes without an extensive recrystallization procedure, with a concomitant decrease in product yield.

Accordingly, it is an object of this invention to provide a process for producing anthranilic acid derivatives which is superior to prior art methods such as that described in Japanese patent application No. 8858/81.

It is another object of this invention to provide an improved method for producing nuclear di-substituted cinnamoylanthranilic acid derivatives with a high purity and yield, which derivatives possess antiallergic properties and thus are useful for treatment of asthma, hay fever, atopic dermatitis and urticaria.

Other objects and advantages of this invention will become apparent from the accompanying description and examples.

DESCRIPTION OF THE INVENTION

This invention provides an improved method for the production of nuclear substituted cinnamoylanthranilic acid derivatives corresponding to the formula:

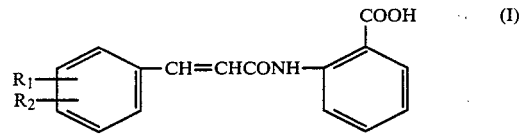

where $R_1$ is hydroxyl and $R_2$ is an alkoxyl substituent containing about 1–3 carbon atoms. The said derivatives possess antiallergic properties, and are useful for treatment of diseases caused by allergies, such as asthma, hay fever, atopic dermatitis and urticaria.

Thus, one or more objects of the present invention are accomplished by the provision of a process which comprises reacting a nuclear di-substituted benzaldehyde corresponding to the formula:

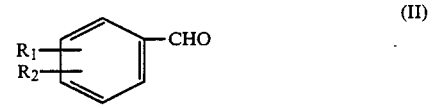

where $R_1$ and $R_2$ are substituents as previously defined, in an inert organic solvent with 2-carboxymalonanilic acid corresponding to the formula:

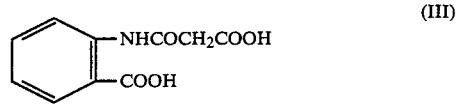

and a cyclic amine corresponding to the formula:

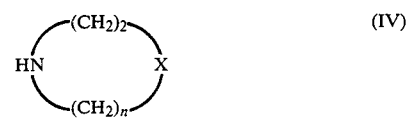

where X is a methylene group or an oxygen atom, n is 1 or 2 with the proviso that n is 2 when X is an oxygen atom, and said cyclic amine is employed in a molar ratio of about 2–10 moles per mole of nuclear substituted benzaldehyde derivative of formula(II) or the 2-carboxymalonanilic acid of Formula(III) above, to produce a crystalline precipitate of an intermediate compound corresponding to the formula:

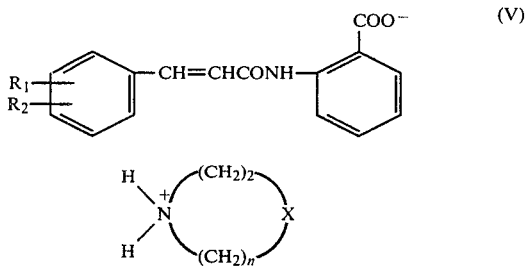

where $R_1$, $R_2$, X and n are as previously defined; and treating the said compound (V) under acidic conditions to yield a product corresponding to formula(I) above.

In the present invention process a specific type of cyclic amine compound is utilized in a molar ratio of 2-10 moles per mole of the starting material of formula(II) or (III) above. By employing a molar excess of the cyclic amine over the benzaldehyde(II) or 2-carboxymalonanilic acid(III) compounds in an inert organic solvent as a reaction medium, the intermediate of formula(V), i.e., the salt of nuclear substituted cinnamoylanthranilic acid derivative and cyclic amine, precipitates as crystals in high yield and purity from the reaction mixture as the reaction proceeds, and thereafter is readily recovered from the reaction mixture. The crystalline compound(V) is substantially free of unreacted materials and byproducts and can be converted easily into the desired free acid product in a high purity form by treatment with an acidic reagent such as a mineral acid.

As demonstrated in the Examples, the optimal yield of high purity crystalline salt intermediate is achieved when the molar ratio of cyclic amine to benzaldehyde(II) or 2-carboxymalonanilic acid(III) is about 3:1.

Thus, by the practice of the present invention process the problems associated with the procedure disclosed in Japanese patent application No. 8858/81 are eliminated, and nuclear substituted cinnamoylanthranilic acid derivatives are prepared efficiently in high yield and purity.

Illustrative of inert organic solvents suitable in the invention process (i.e., solvents with solubility properties which promote crystallization of the intermediate(V) as the reaction proceeds) are benzene, toluene, xylene, ethyl acetate and chloroform. Preferred inert organic solvents are aromatic hydrocarbons such as benzene and toluene. The solvent is employed in a volume which typically will vary between about 1-30 milliliters per gram of benzaldehyde and 2-carboxymalonanilic acid reactants.

The cyclic amine component employed in the invention process possesses a catalytic property for condensing a nuclear di-substituted benzaldehyde derivative and 2-carboxymalonanilic acid, and possesses properties which enhance the formation of insoluble cyclic amine salt of cinnamoylanthranilic acid derivative in an inert solvent medium. Illustrative of the invention cyclic amines are pyrrolidine, piperidine and morpholine. Piperidine is an exceptional cyclic amine for purposes of the present invention process.

Acid reagents suitable for the conversion of the intermediate(V) compound above into the desired compound(I) include inorganic acids such as hydrochloric acid, sulfuric acid, and the like, and organic acids such as acetic acid or p-toluenesulfonic acid. The use of a mineral acid such as hydrochloric acid is preferred.

The nuclear di-substituted benzaldehyde derivatives corresponding to formula(II) which are employed as a starting material are known compounds, and methods of synthesis are described in the chemical literature. Examples of said aldehydes include 2-hydroxy-3-methoxybenzaldehyde; 3-hydroxy-2-methoxybenzaldehyde; 3-hydroxy-4-methoxybenzaldehyde; 4-hydroxy-3-methoxybenzaldehyde; 3-hydroxy-4-propoxybenzaldehyde; 4-hydroxy-3-propoxybenzaldehyde; and the like.

2-Carboxymalonanilic acid used as a starting material is also a known compound, and can be prepared according to the method described in Japanese application No. 43678/74.

Since dehydration and decarboxylation reactions occur simultaneously with the formation of the intermediate compound corresponding to formula(V) above, in a preferred process embodiment the reaction is conducted with continuous removal of water formed during the reaction course.

As a general procedure, a mixture of a benzaldehyde derivative corresponding to formula(II), 2-carboxymalonanilic acid, and 2-10 moles of cyclic amine corresponding to formula(IV) (e.g., piperidine) per mole of the benzaldehyde derivative(II) or 2-carboxymalonanilic acid(III) is dissolved in an inert organic solvent (e.g., benzene or toluene) in a proportion of about 1-3 liters of solvent per mole of benzaldehyde derivative, and then the resultant reaction solution is heated under reflux for a period of about 3-5 hours with continuous removal of water as it is formed during the reaction.

After cooling, the precipitated crystalline salt intermediate is recovered by filtration and dissolved with heating in water. The resultant aqueous solution is added dropwise to a dilute mineral acid solution. The crystalline product which precipitates is collected by conventional means such as filtration, and optionally, recrystallized from an organic solvent to provide the desired product corresponding to formula(I).

It is an advantage of the invention process that the cyclic amine that is utilized can be recovered from the filtrate and recycled in the process.

The following Examples are further illustrative of the present invention. The specific ingredients and processing parameters are presented as being typical, and various modifications can be derived in view of the foregoing disclosure within the scope of the invention.

EXAMPLE I

This Example illustrates the advantages of preparing nuclear substituted cinnamoylanthranilic acid derivatives with a molar excess of cyclic amine in accordance with the present invention process.

A. A solution of 2.54 g of 4-hydroxy-3-methoxybenzaldehyde, 3.8 g of 2-carboxymalonanilic acid, and 4.29 g of piperidine in 17 ml of benzene is heated for 3 hours under reflux with removal of water of reaction. After completion of the reaction, the reaction mixture is cooled and the precipitated crystals are collected by filtration and dried to obtain 6.34 g of piperidinium N-(4-hydroxy-3-methoxycinnamoyl)anthranilate, mp. 188°-189° C. The compound structure is confirmed by elemental analysis, and by IR and NMR spectroscopy.

The molar ratio of piperidine to 4-hydroxy-3-methoxybenzaldehyde in the above preparation is 3:1. The same procedure is employed with 3-hydroxy-4-methoxybenzaldehyde to synthesize piperidinium N-(3-hydroxy-4-methoxycinnamoyl)anthranilate, m.p. 197°-203° C.

The same procedure is employed with different molar ratios of piperidine to 4-hydroxy-3-methoxybenzaldehyde and 3-hydroxy-4-methoxybenzaldehyde, respectively.

The results as summarized in Table I demonstrate the superiority of the present invention process for the production of a high yield of crystalline nuclear substituted cinnamoylanthranilate salt intermediate. Examples II and IV illustrate the conversion of the crystalline piperidinium salts to the desired N-(4-hydroxy-3-methoxycinnamoyl)anthranilic acid and N-(3-hydroxy-4-methoxycinnamoyl)anthranilic acid products.

B. In a manner similar to that described in IA above, comparative runs (Table II) are conducted with different molar ratios of morpholine to 4-hydroxy-3-methoxybenzaldehyde and 3-hydroxy-4-methoxybenzaldehyde, respectively. The crystalline salt intermediates are morpholinium N-(4-hydroxy-3-methoxycinnamoyl)anthranilate (m.p. 183°-185° C.) and morpholinium N-(3-hydroxy-4-methoxycinnamoyl)anthranilate (m.p. 133°-137° C., with decomposition).

Examples III and V illustrate the conversion of the crystalline morpholinium salts of N-(4-hydroxy-3-methoxycinnamoyl)anthranilic acid and N-(3-hydroxy-4-methoxycinnamoyl)anthranilic acid products of the invention.

In a manner similar to that described in IA above, comparative runs (Table III) are conducted with different molar ratios of pyrrolidine to 4-hydroxy-3-methoxybenzaldehyde and 3-hydroxy-4-methoxybenzaldehyde, respectively. The crystalline salt intermediates are pyrrolidinium N-(4-hydroxy-3-methoxycinnamoyl)anthranilate (m.p. 181°-186° C.) and pyrrolidinium N-(3-hydroxy-4-methoxycinnamoyl)anthranilate (m.p. 175°-179° C.).

Examples III and V illustrate the conversion of the crystalline pyrrolidinium salts to the free acid products of the invention.

Similar results are obtained if the benzaldehyde reactant in all of the above described procedures is 3-hydroxy-2-methoxybenzaldehyde or 2-hydroxy-3-methoxybenzaldehyde.

TABLE I

| | | Reactants | | | | |
|---|---|---|---|---|---|---|
| | | 4-hydroxy-3-methoxybenzaldehyde | | | 3-hydroxy-4-methoxybenzaldehyde | |
| Amine | mole | amount of the precipitates or the residue | purity of the precipitates or the residue | net weight of the resultant product | amount of the precipitates or the residue | purity of the precipitates or the residue | net weight of the resultant product |
| | | resultant product: $C_{22}H_{26}O_5N_2$ molecular weight: 398.422 theoretical amount: 6.65 g | | | resultant product: $C_{22}H_{26}O_5N_2$ molecular weight: 398.422 theoretical amount: 6.65 g | | |
| HN⟨⟩ | 0.1 | 5.92 g | 14.6% | 0.86 g (12.93%) | 5.86 g | 27.6% | 1.62 g (24.36%) |
| | 1.0 | 6.85 g | 61.5% | 4.21 g (63.35%) | 6.05 g | 68.8% | 4.16 g (62.59%) |
| | 3.0 | 6.34 g | 101.9% | 6.34 g (95.34%) | 6.25 g | 98.5% | 6.16 g (92.63%) |
| | 5.0 | 6.31 g | 97.7% | 6.16 g (92.70%) | 6.17 g | 94.3% | 5.82 g (87.49%) |
| | 7.0 | 6.02 g | 101.2% | 6.02 g (90.53%) | 5.48 g | 99.9% | 5.47 g (82.26%) |
| | 10.0 | 5.63 g | 97.7 | 5.50 g (82.7%) | 5.52 g | 99.3% | 5.48 g (82.43%) |

TABLE II

| | | Reactants | | | | | |
|---|---|---|---|---|---|---|---|
| | | 4-hydroxy-3-methoxybenzaldehyde (MeO, HO — CHO) | | | 3-hydroxy-4-methoxybenzaldehyde (HO, MeO — CHO) | | |
| Amine | mole | amount of the precipitates or the residue | purity of the precipitates or the residue | net weight of the resultant product | amount of the precipitates or the residue | purity of the precipitates or the residue | net weight of the resultant product |
| | | resultant product: $C_{21}H_{24}O_6N_2$ molecular weight: 400.416 theoretical amount: 6.687 g | | | resultant product: $C_{21}H_{24}O_6N_2$ molecular weight: 400.416 theoretical amount: 6.687 g | | |
| HN⌒O (morpholine) | 0.1 | 5.42 g | 17.9% | 0.97 g (14.51%) | 6.00 g | 15.6% | 0.94 g (14.00%) |
| | 1.0 | 7.43 g | 42.5% | 3.16 g (47.22%) | 7.26 g | 63.6% | 4.62 g (69.04%) |
| | 3.0 | 6.56 g | 84.0% | 5.51 g (82.40%) | 6.68 g | 75.6% | 5.05 g (75.52%) |
| | 5.0 | 5.96 g | 81.8% | 4.88 g (72.98%) | 8.32 g | 22.1% | 1.84 g (27.52%) |
| | 7.0 | 6.07 g | 50.1% | 3.04 g (45.48%) | 6.27 g | 19.5% | 1.22 g (18.24%) |
| | 10.0 | 5.71 g | 33.6% | 1.92 g (28.69%) | 5.79 g | 25.7% | 1.49 g (22.28%) |

TABLE III

| | | Reactants | | | | | |
|---|---|---|---|---|---|---|---|
| | | 4-hydroxy-3-methoxybenzaldehyde (MeO, HO — CHO) | | | 3-hydroxy-4-methoxybenzaldehyde (HO, MeO — CHO) | | |
| Amine | mole | amount of the precipitates or the residue | purity of the precipitates or the residue | net weight of the resultant product | amount of the precipitates or the residue | purity of the precipitates or the residue | net weight of the resultant product |
| | | resultant product: $C_{21}H_{24}O_5N_2$ molecular amount: 384.416 theoretical amount: 6.419 g | | | resultant product: $C_{21}H_{24}O_5N_2$ molecular amount: 384.416 theoretical amount: 6.419 g | | |
| HN (pyrrolidine) | 0.1 | 5.39 g | 18.7% | 1.01 g (15.73%) | 5.94 g | 18.4% | 1.09 g (16.98%) |
| | 1.0 | 7.41 g | 52.4% | 3.88 g (60.49%) | 7.07 g | 67.4% | 4.77 g (74.24%) |
| | 3.0 | 6.36 g | 98.2% | 6.25 g (97.37%) | 6.30 g | 86.2% | 5.43 g (84.59%) |
| | 5.0 | 6.19 g | 97.1% | 6.01 g (93.64%) | 5.91 g | 85.3% | 5.04 g (78.54%) |
| | 7.0 | 4.90 g | 93.4% | 4.58 g (71.35%) | 5.52 g | 63.7% | 3.52 g (54.84%) |
| | 10.0 | 5.78 g* | 85.9 | 4.27 g (77.35%) | 2.67 g* | 85.9% | 2.29 g (35.73%) |

*Resultant product did not readily crystallize.

EXAMPLE II

A 10 g quantity of piperidinium N-(4-hydroxy-3-methoxycinnamoyl)anthranilate is dissolved in a mixture of 80 ml of water and 60 ml of methyl alcohol with heating, and the resultant solution is added dropwise to 85 ml of diluted hydrochloric acid (5 ml of conc. hydrochloric acid and 80 ml of water) with stirring. The precipitated crystals which form are collected by filtration, washed with water and then dried at 90°-100° C. under reduced pressure for 3 hours to yield N-(4-hydroxy-3-methoxycinnamoyl)anthranilic acid (98.5% yield), m.p. 230°-233° C. The compound structure is confirmed by elemental analysis, and by IR and NMR spectroscopy.

EXAMPLE III

A 10 g quantity of morpholinium N-(4-hydroxy-3-methoxycinnamoyl)anthranilate is dissolved in a mixture of 80 ml of water and 60 ml of methyl alcohol with heating, and the resultant solution is added dropwise to 85 ml of diluted hydrochloric acid (5 ml of conc. hydrochloric acid and 80 ml of water) with stirring. The precipitated crystals which form are collected by filtration, washed with water and then dried at 90°-100° C. under reduced pressure for 3 hours to yield N-(4-hydroxy-3-methoxycinnamoyl)anthranilic acid (82.5% yield). The compound is confirmed as identical to that obtained in Example II.

Similar results are obtained with pyrrolidinium N-(4-hydroxy-3-methoxycinnamoyl)anthranilate.

EXAMPLE IV

A 10 g quantity of piperidinium N-(3-hydroxy-4-methoxycinnamoyl)anthranilate is dissolved in a mixture of 80 ml of water and 80 ml of methyl alcohol with heating, and the resultant solution is added dropwise to 85 ml of diluted hydrochloric acid (5 ml of conc. hydrochloric acid and 80 ml of water) with stirring. The precipitated crystals which form are collected by filtration, washed with water and then dried at 90°–100° C. under reduced pressure for 3 hours to yield N-(3-hydroxy-4-methoxycinnamoyl)anthranilic acid (97.0% yield), m.p. 219°–222° C. The compound structure is confirmed by elemental analysis, and by IR and NMR spectroscopy.

EXAMPLE V

A 10 g quantity of morpholinium N-(3-hydroxy-4-methoxycinnamoyl)anthranilate is dissolved in a mixture of 80 ml of water and 60 ml of methyl alcohol with heating, and the resultant solution is added dropwise to 85 ml of diluted hydrochloric acid (5 ml of conc. hydrochloric acid and 80 ml of water) with stirring. The precipitated crystals which form are collected by filtration, washed with water and then dried at 90°–100° C. under reduced pressure for 3 hours to yield N-(3-hydroxy-4-methoxycinnamoyl)anthranilic acid (74.0% yield). The compound is confirmed as identical to that obtained in Example IV.

Similar results are obtained with pyrrolidinium N-(3-hydroxy-4-methoxycinnamoyl)anthranilate.

What is claimed is:

1. A process for the production of a nuclear substituted cinnamoylanthranilic acid derivative corresponding to the formula:

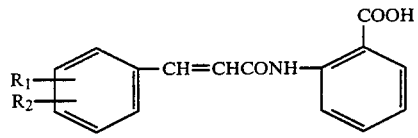

where $R_1$ is hydroxy and $R_2$ is an alkoxyl group containing about 1–3 carbon atoms, which process comprises (1) reacting in an inert organic solvent medium a nuclear substituted benzaldehyde derivative corresponding to the formula:

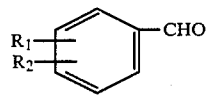

where $R_1$ and $R_2$ are as previously defined, with 2-carboxymalonanilic acid and a cyclic amine corresponding to the formula:

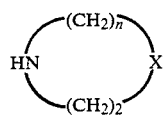

where X is a methylene group or an oxygen atom, n is 1 or 2 with the proviso that n is 2 when X is an oxygen atom, and said cyclic amine is employed in a molar ratio of about 2–10 moles per mole of substituted benzaldehyde derivative reactant or 2-carboxymalonanilic acid reactant, to produce a crystalline precipitate of an intermediate compound corresponding to the formula:

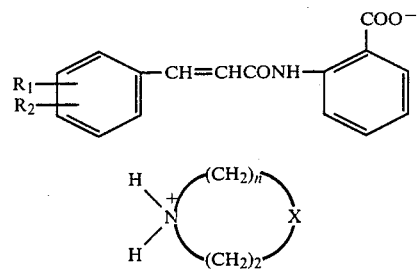

where $R_1$, $R_2$, n and X are as previously defined; and (2) treating the intermediate compound with an acidic reagent to yield a nuclear substituted cinnamoylanthranilic acid product corresponding to the first formula above.

2. A process in accordance with claim 1 wherein water of reaction is removed from the reaction zone during the heating period.

3. A process in accordance with claim 1 wherein the inert organic solvent is an aromatic hydrocarbon.

4. A process in accordance with claim 1 wherein the inert organic solvent is benzene or toluene.

5. A process in accordance with claim 1 wherein the benzaldehyde reactant is 4-hydroxy-3-methoxybenzaldehyde.

6. A process in accordance with claim 1 wherein the benzaldehyde reactant is 3-hydroxy-4-methoxybenzaldehyde.

7. A process in accordance with claim 1 wherein the cyclic amine is piperidine.

8. A process in accordance with claim 1 wherein the cyclic amine is morpholine.

9. A process in accordance with claim 1 wherein the cyclic amine is pyrrolidine.

10. A process in accordance with claim 1 wherein the nuclear substituted cinnamoylanthranilic acid product is N-(4-hydroxy-3-methoxycinnamoyl)anthranilic acid.

11. A process in accordance with claim 1 wherein the nuclear substituted cinnamoylanthranilic acid product is N-(3-hydroxy-4-methoxycinnamoyl)anthranilic acid.

12. A process for the production of a nuclear substituted cinnamoylanthranilic acid salt which comprises reacting in an inert organic solvent medium a nuclear substituted benzaldehyde derivative corresponding to the formula:

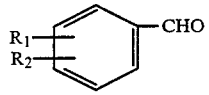

where $R_1$ is hydroxy and $R_2$ is an alkoxy group containing about 1–3 carbon atoms, with 2-carboxymalonanilic acid and a cyclic amine corresponding to the formula:

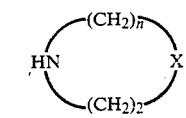

where x is a methylene group or an oxygen atom, n is 1 or 2 with the proviso that n is 2 when X is an oxygen atom, and said cyclic amine is employed in a molar ratio of about 2–10 moles per mole of substituted benzaldehyde derivative reactant or 2-carboxymalonanilic acid reactant, to produce a crystalline precipitate of a salt product corresponding to the formula:
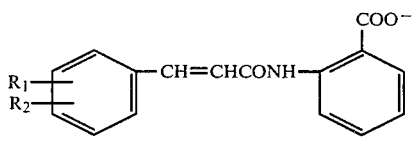
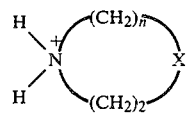
where $R_1$, $R_2$, n and X are as previously defined.
* * * * *